United States Patent [19]

Petty

[11] 4,217,294
[45] Aug. 12, 1980

[54] METHOD FOR PRODUCING MERCAPTAN-CONTAINING ORGANOSILICON COMPOUNDS

[75] Inventor: Herbert E. Petty, Bethel, Conn.

[73] Assignee: Union Carbide Corporation, New York, N.Y.

[21] Appl. No.: 25,658

[22] Filed: Mar. 30, 1979

[51] Int. Cl.² .............................. C07F 7/10; C07F 7/18
[52] U.S. Cl. ...................................... 556/419; 556/429
[58] Field of Search .................................. 260/448.8 R

[56] References Cited

U.S. PATENT DOCUMENTS

| | | | |
|---|---|---|---|
| 3,590,065 | 6/1971 | Rakus et al. | 260/448.8 R |
| 3,631,194 | 12/1971 | LeGrow | 260/448.8 R X |
| 3,642,855 | 2/1972 | Berger | 260/448.8 R |
| 3,957,844 | 5/1976 | Mui | 260/448.8 R X |
| 4,012,403 | 3/1977 | Mui | 260/448.8 R |

OTHER PUBLICATIONS

Gilbert et al., "J. of Chem. Eng. Data," 13, p. 130, 1968.

*Primary Examiner*—Paul F. Shaver
*Attorney, Agent, or Firm*—Richard J. Gallagher

[57] ABSTRACT

A two-stage process for producing gamma-mercaptopropyltrialkoxysilane which comprises reacting beta-cyanoethyltrialkoxysilane with hydrogen sulfide in the presence of an amide to form a novel gamma-trialkoxysilylthiopropionamide intermediate followed by reducing said intermediate with hydrogen in the presence of a transition metal polysulfide.

8 Claims, No Drawings

METHOD FOR PRODUCING MERCAPTAN-CONTAINING ORGANOSILICON COMPOUNDS

BACKGROUND OF THE INVENTION

1. Field of the Invention

This invention relates to a novel process for making mercaptopropylalkoxysilanes.

2. Description of the Prior Art

Mercapto-substituted silicon compounds are known in the art. They had been made primarily by two processes. One involves the addition of hydrogen sulfide to an ethylenically unsaturated radical bonded directly to silicon. This is illustrated by the reaction of a large excess (e.g. greater than 400%) of hydrogen sulfide with a vinyl substituted silane. The other common method for manufacture of mercapto-substituted silicone compounds involves the reaction of an alkali metal mercaptide with a choroalkyl silicon compound, which results in the formation of sodium chloride by-product.

Recently, U.S. Pat. No. 4,012,403 disclosed a synthesis of mercapto-substituted silicon compounds which avoids the necessity of using such a large excess of hydrogen sulfide and which does not result in the formation of a corrosive by-product such as sodium chloride. The synthesis described in said patent is based upon the development of a method for reducing beta-cyanoethyltrialkoxysilane by reaction with sulfur. It was found that, by reacting one mole of beta-cyanoethyltrialkoxysilane at high pressure and elevated temperatures with a least three moles of hydrogen and at least one mole of sulfur in the presence of a transition metal polysulfide catalyst, one could obtain high yields of the corresponding mercaptopropyltrialkoxysilane.

SUMMARY OF THE INVENTION

It has now been found that beta-cyanoethyltrialkoxysilane can be advantageously converted to the corresponding mercaptopropyltrialkoxysilane via the trialkoxysilylthiopropionamide in a two stage process. The advantages of the two stage process, relative to the one stage process of U.S. Pat. No. 4,012,403, include: (1) greater control of stoichiometry of the gases consumed (i.e. one gas is consumed per stage) and (2) increase in production yield in a reactor of a given pressure rating due to lower total pressure per mole of reactants.

The present invention, then, relates to a process for producing gamma-mercaptopropyltrialkoxysilane which comprises first, reacting beta-cyanoethyltrialkoxysilane with hydrogen sulfide in the presence of an amine to form a novel beta-trialkoxysilylthiopropionamide intermediate, and second, reducing the novel beta-trialkoxysilylthiopropionamide with hydrogen in the presence of a transition metal polysulfide.

DESCRIPTION OF THE PREFERRED EMBODIMENTS

In the first step of the two stage process of this invention, beta-cyanoethyltrialkoxysilane is converted with hydrogen sulfide in the presence of an amine to the corresponding beta-(thiocarboxamido) ethyltrialkoxysilane. The preparation of thioamides based on the alkali-catalyzed reaction of nitriles with hydrogen sulfide or thiols is well-established in the literature. However, the yield of thioamide is greatly influenced by the nature of the starting nitrile. Aromatic nitriles generally react rapidly in the presence of a base, forming excellent yields of the corresponding thioamide. Aliphatic nitriles usually add hydrogen sulfide with greater difficulty. The amine-catalyzed condensation of hydrogen sulfide with silicon-containing aliphatic nitriles was found to be a facile method of preparation of the novel class of intermediates of the formula

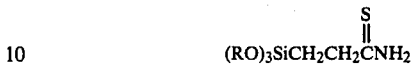

where R is an alkyl, and preferably a $C_1$–$C_4$ lower alkyl, group.

In converting beta-cyanoethyltrialkoxysilane to beta-(thiocarboxamido)-ethyltrialkoxysilane, the beta-cyanoethyltrialkoxysilane, e.g. $(C_2H_5O)_3SiCH_2CH_2CN$, is reacted with the hydrogen sulfide in the presence of an amide catalyst, e.g. a secondary amine such as diethylamine. An aprotic reaction solvent in which hydrogen sulfide is soluble, such as dimethylformamide, may be utilized. The solvent is necessary only in low pressure reactions to maintain a sufficient concentration of hydrogen sulfide for an appreciable reaction rate. However, a solvent is not necessary in a closed system, allowing simply the stoichiometric quantity of hydrogen sulfide to be added initially. The quantity of hydrogen sulfide consumed by the reaction can readily be monitored by the decrease in the pressure of the closed system; this provides a simple measure of reaction completion. The preferred reaction temperature is 50°–65° C. At temperatures exceeding 100° C., a reverse reaction takes precedence in the presence of the amine catalyst: i.e., the silicon-containing thioamide liberates hydrogen sulfide and re-forms the starting nitrile.

The second stage of the two stage process of this invention embodies a reaction which has been heretofore unknown. In this stage, beta-(thiocarboxamido)ethyltrialkoxysilane is reacted with hydrogen in the presence of a transition metal polysulfide catalyst to form gamma-mercaptopropyltrialkoxysilane.

It is known that thioamide groups can be reduced with such conventional reducing agents as zinc in acid solution, lithium hydride, or lithium aluminum hydride. (True catalytic processes under hydrogen pressure have not been reported, due, probably, to poisoning of the catalyst by the sulfur function.) However, such reductions of thioamide groups result in the formation of an amine. In contrast, it has now been found that transition metal polysulfides, such as those developed for the reductive thiolation process of U.S. Pat. No. 4,012,403 (not being subject to such poisoning), may be utilized to reduce thioamide groups not to amines but to mercaptans.

Thus, a key feature of the present invention is a process for preparing gamma-mercaptopropyltrialkoxysilane which comprises reacting beta-(thiocarboxamido)ethyltrialkoxysilane with hydrogen, in a pressure reactor, at a temperature between about 100° C. and about 300° C., in the ratio of at least 2 moles of hydrogen for each mole of the silane, and in the presence of about 0.01 to about 10 weight percent, based on the weight of the silane and hydrogen, of a transition metal polysulfide. A preferred embodiment of this process step comprises reacting beta-(thiocarboxamido)ethyltrialkoxysilane with at least two moles of hydrogen, in a pressure reactor wherein there is present about 2.5 weight percent of cobalt trisulfide catalyst at a temperature of about 200° C.

EXAMPLES

The working examples which follow are presented to illustrate the practice of the present invention. They are not intended to be, and should not be construed as, limiting the scope of the invention.

EXAMPLE I

Preparation of beta-triethoxysilylthiopropionamide

Laboratory Scale

Into a clean, dry 300 milliliter high pressure reaction vessel was added 200 grams (0.92 moles) of beta-cyanoethyltriethoxysilane and 10 grams of diethylamine. The reactor was cooled to the temperature of solid carbon dioxide, and 42.0 grams (1.3 moles) of hydrogen sulfide was added via a calibrated metering system. The reactor was placed in a rocker and with agitation was heated to 60° C. for 5 hours. The pressure of the system increased to a maximum of 140 psig and decreased to 70 psig when the reaction was terminated. The final pressure at ambient temperature was 30 psig. The yield of crude beta-triethoxysilylthiopropionamide product was 258.4 grams. Analysis of the product mixture indicated 19 mg/g or 16% unreacted beta-cyanoethyltriethoxysilane.

EXAMPLE II

Preparation of beta-triethoxysilylthiopropionamide

Pilot Plant Scale

Utilizing a 15 gallon high pressure stainless steel system, 80 pounds of beta-cyanoethyltriethoxysilane and 8 pounds of diethylamine were added initially. With a diptube, 12 pounds of hydrogen sulfide was charged into the reactor while cooling was maintained. The reactor was then heated to 60° C. with stirring for 6 hours. The residual hydrogen sulfide (80 psig) was carefully vented into a caustic scrubber and the product thioamide (94 pounds) was collected. The product, analyzed by InfraRed Spectroscopy, contained 5% unreacted nitrile.

EXAMPLE III

Preparation of beta-triethoxysilylthiopropionamide

In Dimethylformamide

Into a four necked 500 milliliter flask equipped with a mechanical agitator, thermometer, thermostatted heating mantel, hydrogen sulfide inlet tube with calibrator flowmeter, and condenser was added 250 milliliters of a solution prepared by diluting 108.5 grams of beta-cyanoethyltriethoxysilane and 10.9 grams of diethylamine to 500 milliliters (351.8 grams) with dimethylformamide (equivalent to 1.0 molar solution of beta-cyanoethyltriethoxysilane). The solution was heated to 65° and maintained at 65° during the course of reaction. Hydrogen sulfide was added at a rate of 0.25 g/minute during the course of the experiment. Samples taken periodically, measuring consumption of nitrile by InfraRed Spectroscopy (IR) as a measure of the extent of reaction, are summarized below.

| Time (minutes) | Temperature °C. | Results (quantative IR determination) |
|---|---|---|
| 0 | 65 | 0.96 moles CN/liter |
| 15 | 65 | 0.86 moles CN/liter |
| 30 | 65 | 0.73 moles CN/liter |
| 45 | 65 | 0.73 moles CN/liter |
| 60 | 65 | 0.69 moles CN/liter |
| 90 | 65 | 0.60 moles CN/liter |
| 120 | 65 | 0.55 moles CN/liter |
| 150 | 65 | 0.45 moles CN/liter |
| 192 | 65 | 0.38 moles CN/liter |

EXAMPLE IV

Preparation of gamma-mercaptopropyltriethoxysilane

High Pressure

Into a clean, dry 300 cubic centimeter high pressure reactor were added 58 grams (0.23 moles) of beta-triethoxysilylthiopropionamide product (containing 14% beta-cyanoethyltriethoxysilane starting material) and 2.5 weight percent of cobalt trisulfide. The reactor was sealed, pressurized to 1100 psig with hydrogen, and placed in a rocker. The vessel was heated to 200° C. internal temperature and maintained at that temperature for 5 hours with agitation while the pressure increased to a maximum of 1750 psig. The final pressure at elevated temperature was 1500 psig and at ambient temperature was 600 psig (indicating that hydrogen was consumed by the reaction.) This procedure yielded 59% of the desired gamma-mercaptopropyltriethoxysilane.

EXAMPLE V

Preparation of gamma-mercaptopropyltriethoxysilane

Continuous Hydrogen Feed

Into a clean, dry 300 cubic centimeter high pressure reactor were added 150 grams (0.60 moles) of beta-triethoxysilylthiopropionamide product (Example II pilot plant lot containing 5% beta-cyanoethyltriethoxysilane starting material) and 2.5 weight percent of cobalt trisulfide. The reactor was sealed, initially pressurized to 600 psig with hydrogen and placed in a rocker. The vessel was heated to 195° C. internal temperature which raised the hydrogen pressure to 1100 psig. Heating was maintained for 8 hours with agitation. Hydrogen was continuously fed into the reactor to maintain the hydrogen pressure at about 1000 psig. The pressure never exceeded 1100 psig. The pressure at the end of the reaction was 575 psig. The reaction produced the desired gamma-mercaptopropyltriethoxysilane.

EXAMPLE VI

Preparation of gamma-mercaptopropyltriethoxysilane

Rhenium Sulfide Catalyst

Into a clean, dry 300 cubic centimeter high pressure reactor were added 58 grams (0.23 moles) of beta-triethoxysilylthiopropionamide product (Example II pilot plant lot containing 5% beta-cyanoethyltriethoxysilane starting material), 1.45 grams (2.5 weight percent) of rhenium heptasulfide catalyst ($Re_2S_7 \cdot 2H_2O$), and 12 grams ethanol rinse. The reactor was sealed, initially pressurized to 800 psig with hydrogen, and placed in a rocker. The vessel was heated with agitation for 4 hours to a maximum pressure of 1000 psig. After cooling to ambient temperature, the pressure was 0 psig, indicating that hydrogen was consumed by the reaction. The reaction had produced gamma-mercaptopropyltriethoxysilane.

Various modifications and variations of this invention will be obvious to a worker skilled in the art and it is to be understood that such modifications and variations are to be included within the purview of this application and the spirit and scope of the appended claims.

What is claimed is:

1. A process for preparing gamma-mercaptopropyltrialkoxysilane which comprises
   reacting beta-cyanoethyltrialkoxysilane with about one mole of hydrogen sulfide in the presence of an amine catalyst at a temperature not exceeding 100° C. to form a beta-(thiocarboxamido) ethyltrialkoxysilane intermediate and subsequently
   reacting the beta-(thiocarboxamido) ethyltrialkoxysilane with hydrogen under pressure, at a temperature between about 100° C. and about 300° C., in the ratio of at least two moles of hydrogen for each mole of the silane, and in the presence of about 0.01 to about 10 weight percent, based on the weight of the silane and hydrogen, of a transition metal polysulfide catalyst to form a gamma-mercaptopropyltrialkoxysilane.

2. A process as in claim 1 wherein the beta-(thiocarboxamido)ethyltrialkoxysilane is beta-(thiocarboxamido)ethyltriethoxysilane.

3. A process as in claim 1 wherein the reaction temperature is about 200° C.

4. A process as in claim 1 wherein the weight percent of the catalyst is about 2.5.

5. A process as in claim 1 wherein the catalyst is cobalt trisulfide.

6. A process for preparing gamma-mercaptopropyltriethoxysilane which comprises reacting beta-(thiocarboxamido)ethyltriethoxysilane with hydrogen, in a pressure reactor, at a temperature of about 200° C., wherein there is present about 2.5 weight percent of cobalt trisulfide.

7. A compound of the formula

wherein R is an alkyl group.

8. A compound as in claim 7 wherein R is ethyl.